United States Patent [19]

Maggi et al.

[11] Patent Number: 6,149,940
[45] Date of Patent: Nov. 21, 2000

[54] TABLET WITH CONTROLLED RELEASE OF ALFUZOSINE CHLORHYDRATE

[75] Inventors: Lauretta Maggi, Pavia; Ubaldo Conte, Busto Arisizio., both of Italy; Pascal Grenier; Guy Vergnault, both of Saint Louis, France; Alain Dufour, Paris, France; François Xavier Jarreau, Versailles, France; Clemence Rauch-Desanti, Ozoire la Ferrière, France

[73] Assignees: Synthelabo, Le Plessis-Robinson, France; Jagotec AB, Hergiswil, Switzerland

[21] Appl. No.: 09/147,581

[22] PCT Filed: Aug. 22, 1997

[86] PCT No.: PCT/FR97/01515

§ 371 Date: Apr. 26, 1999

§ 102(e) Date: Apr. 26, 1999

[87] PCT Pub. No.: WO98/08515

PCT Pub. Date: Mar. 5, 1998

[30] Foreign Application Priority Data

Aug. 29, 1996 [FR] France ................................... 96 10551
Apr. 10, 1997 [FR] France ................................... 97 04386

[51] Int. Cl.[7] ................................ A61K 9/24; A61K 9/28; A61K 9/22
[52] U.S. Cl. ..................... 424/472; 424/468; 424/474; 514/772.3; 514/777; 514/778; 514/779; 514/773; 514/781; 514/784; 514/785

[58] Field of Search .................... 424/468, 469, 424/470, 472, 474, 465

[56] References Cited

U.S. PATENT DOCUMENTS

| | | | |
|---|---|---|---|
| 4,661,491 | 4/1987 | Regnier | 514/260 |
| 4,839,177 | 6/1989 | Colombo et al. | 424/482 |
| 5,422,123 | 6/1995 | Conte et al. | 424/479 |
| 5,589,190 | 12/1996 | Andrieu et al. | 424/462 |

FOREIGN PATENT DOCUMENTS

WO94/27582 12/1994 WIPO.

*Primary Examiner*—James M. Spear
*Attorney, Agent, or Firm*—Jacobson, Price, Holman & Stern, PLLC

[57] ABSTRACT

Pharmaceutical tablet which consists of:
a) a first layer having the property of swelling considerably and quickly on contact with aqueous biological fluids, the first layer being produced by compression of a mixture or of a granulate comprising hydrophilic polymers, and
b) a second layer adjacent to the first layer being formulated with hydrophilic polymers and with other auxiliary substances in order to give the preparation suitable properties of compressibility and in order to allow the release of alfuzosin hydrochloride within a predetermined time period.

23 Claims, 2 Drawing Sheets

TABLET WITH CONTROLLED RELEASE OF ALFUZOSINE CHLORHYDRATE

This applicatin is a 371 of PCT/FR97/01515 filed Aug. 27, 1997.

The present invention relates to a tablet with controlled release of alfuzosin hydrochloride and to a pharmaceutical composition containing one or more tablets.

Alfuzosin hydrochloride is an active substance that is known in the treatment of benign hypertrophy of the prostate. There is a wealth of data and experimental studies regarding the activity of the product. In particular, there is a large amount of data regarding the bioavailability of the product and the pharmacokinetics of the active substance. Indeed, it is an active substance which has a relatively short half-life and a more intense absorption at the duodenum-jejunum level, but the size of which decreases along the intestinal tract. Consequently, for an optimum effect, the administration of alfuzosin hydrochloride as conventional tablets (with rapid disintegration and dissolution) must be carried out several times a day. For these reasons, alfuzosin hydrochloride is a candidate for the production of a pharmaceutical preparation with controlled release in the promixal upper parts of the tract (duodenum and jejunum).

In the pharmaceutical field, noteworthy progress has been made in recent years in the production of increasingly improved systems for the release of active substances, which are capable of releasing the active substances conveyed per se according to kinetics and modes of release designed to allow optimum therapeutic effects.

Prolonged-release forms (or delayed-effect preparations) are characterized in that they convey a markedly larger amount of medicinal product than traditional pharmaceutical preparations, so as to allow the dosage to be simplified. That is to say that the administration decreases from two, three or more times a day to only one administration of a pharmaceutical preparation (or therapeutic system) capable of providing satisfactory therapeutic cover throughout the day.

Preparations of this type have been used and marketed for a long time, among which mention should be made of: chronoids, microcapsules and micro-matrices, tablets generically defined as "delayed-effect" tablets, gastro-resistent tablets and more complex preparations such as hydrophilic matrices which break down and/or swell. Recently, more refined therapeutic systems have been produced, for example so-called "reservoir" systems and the Geomatrix® systems as described in U.S. Pat. Nos. 4,839,177 and 5,422,123.

Most of these novel therapeutic systems are capable of releasing the active substance conveyed per se, at a constant rate (that is to say according to zero-order kinetics) up to complete release of the active substance, independently of the pH conditions of the gastrointestinal tract, and thus uniformly along the gastrointestinal tract. It results therefrom that these systems may be applied widely in the case of administration of medicinal products that are absorbed uniformly in the gastrointestinal tract. However, these pharmaceutical systems may have major drawbacks in the case where active substances per se would be conveyed, such as alfuzosin, having a more intense absorption at the duodenum-jejunum level which decreases thereafter in the tract. Indeed, in this case, only a very limited amount of the active substance conveyed may be absorbed and thus exert the desired therapeutic activity, whereas most of the medicinal product released by the pharmaceutical preparation cannot be absorbed since, in lower portions of the gastrointestinal tract, the biological barriers are relatively incapable of allowing the medicinal product to pass.

The subject of the present patent application is a tablet with controlled release of alfuzosin hydrochloride, which overcomes the drawbacks mentioned above.

Figure 1:
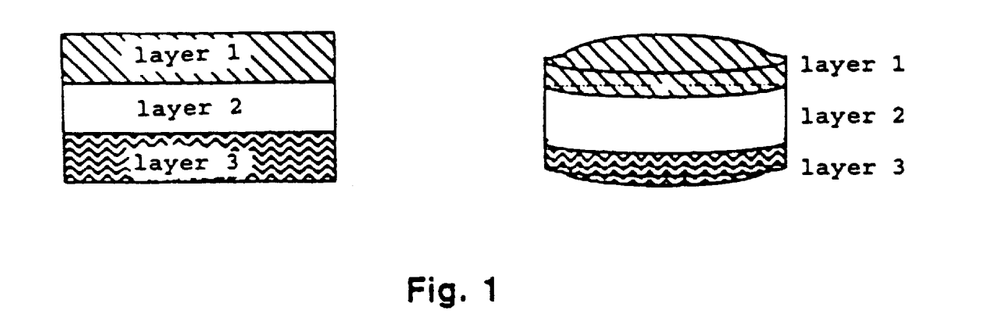
FIG. 1 presents an embodiment of the invention comprising a tablet with three layers as described above.

The invention consists of a pharmaceutical tablet containing two or three layers, characterized in that it has the following structure:

a) a first layer 1 having the property of swelling considerably and quickly on contact with aqueous biological fluids, the said layer being produced by compression of a mixture or of a granulate comprising hydrophilic polymers constituting from 5.0 to 90% and preferably from 10 to 85% of the weight of the layer, b) a second layer 2 adjacent to the first layer, in which the alfuzosin hydrochloride is conveyed, this layer being formulated with hydrophilic polymers and with other auxiliary substances, in order to give the preparation suitable properties of compressibility and in order to allow the release of alfuzosin hydrochloride within a predetermined time period, c) and optionally a third layer 3 obtained by compression and applied to the layer 2, generally consisting in particular of hydrophilic polymers which gel and/or swell and which may then optionally be broken down and having a barrier function which modifies the release of the alfuzosin hydrochloride from the layer 2, the layer 3 being primarily highly impervious to passage of the active substance.

Figure 2:
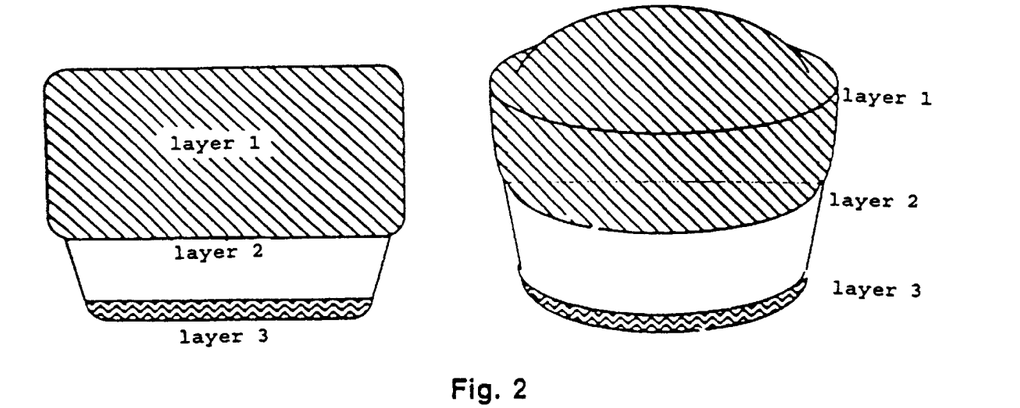

The invention is characterized in that on contact with gastric juices, after rapid and considerable swelling of at least one of the layers 1 or 3, as well as by the possible swelling of the layer 2, the pharmaceutical preparation increases considerably in volume; thus, the pharmaceutical preparation remains in the stomach for longer. In this way, most of the alfuzosin hydrochloride contained may be absorbed in a controlled manner in that portion of the gastrointestinal tract which has the highest capacity for absorption.

The layers 1 and 3 may have an identical composition and identical functional properties or they may have a different composition and different properties.

When the layers 1 and 3 have identical functional properties and compositions, they may differ by their amounts and their thicknesses applied to the layer 2.

At least one of the layers 1 and 3 acts as a barrier, that is to say that it is primarily highly impervious to passage of the alfuzosin hydrochloride contained in the layer 2 and at least one of the layers is characterized in that it swells quickly, that is to say that it quickly increases in volume.

Another embodiment of the pharmaceutical preparation is characterized in that the tablet containing 3 layers is formed of a first layer 1 as described above, that is to say that its sole function is to increase considerably in volume on contact with aqueous liquids, a second layer 2 conveying some of the alfuzosin hydrochloride which has to be released within a predetermined time period, and a third layer 3 in which some of the alfuzosin hydrochloride is conveyed, formulated such that it can be released immediately on contact with gastric juices.

The amount of alfuzosin hydrochloride carried in the tablet is between 2.5 and 50 mg.

The polymeric substances which are used in the layers 1 and 3, and which may also be used in the layer 2, are biocompatible and have hydrophilic properties. They are slowly soluble and/or slowly gelable and/or swell rapidly or at a different rate in aqueous liquids and then may optionally be broken down; they are chosen from the following group:

hydroxymethylcellulose, hydroxyethyl-cellulose, hydroxypropylmethylcellulose having a molecular weight of from 1000 to 4,000,000, hydroxypropylcellulose having a molecular weight of from 2000 to 2,000,000, carboxyvinyl polymers, chitosans, mannans, galactomannans, xanthans, carrageenans, amylose, alginic acid, its salts and its derivatives, pectins, acrylates, methacrylates, acrylic/methacrylic copolymers, polyanhydrides, polyamino acids, poly(methyl vinyl ether/maleic anhydride) polymers, polyvinyl alcohols, glucans, scleroglucans, carboxymethylcellulose and its derivatives, ethylcellulose, methylcellulose and, in general, hydrophilic cellulose derivatives.

The content of hydrophilic polymers may range from 5 to 90% relative to the total weight of the layer, but preferably from 10 to 85% and more particularly from 20 to 80%.

In order to promote a rapid and considerable increase in the volume of the pharmaceutical preparation, during the preparation of the layers 1 and 3, with the hydrophilic polymers mentioned above, it is possible to use hydrophilic products and/or excipients capable of promoting wetting of the layers, in this way facilitating interaction between the components of the said layer and the biological fluids with which the layer comes into contact. These hydrophilic excipients are preferably chosen from the groups of so-called "super disintegrating" excipients comprising crosslinked polyvinylpyrrolidone, hydroxypropylcellulose and hydroxypropylmethylcellulose having a molecular weight form 1,000 to 100,000, crosslinked sodium carboxymethylcellulose, carboxymethyl starch and its salts, and divinylbenzene/potassium methacrylate copolymer.

These substances constitute from 1 to 50% of the weight of the layer and preferably from 10 to 30%.

It is moreover possible also to use surfactants (anionic, cationic and nonionic surfactants) which, by facilitating wetting, allow a more rapid interaction between the dissolution medium (or gastric fluid) and the tablet, thereby allowing much faster wetting and swelling of the pharmaceutical preparation, preferably of the layer in which this hydration-modifying component is conveyed. In the group of substances possessing these properties, mention may be made of products such as sodium lauryl sulphate, sodium ricinoleate, sodium tetradecyl sulphate, sodium dioctyl sulphosuccinate, cetomagrogol, poloxamer, glyceryl monostearate, polysorbates, sorbitan monolaurate, lecithins or any other pharmaceutically acceptable surfactant.

In addition, other hydration-modifying elements may be used, these being chosen from the following group of substances:

hydrophilic diluents such as mannitol, lactose, starches of various origins, sorbitol, xylitol, microcrystalline cellulose and/or substances which, in general, promote the penetration of water or of aqueous fluids into the pharmaceutical preparation, hydrophobic diluents such as glyceryl monostearate, palmitates, hydrogenated or unhydrogenated plant oils such as hydrogenated castor oil, waxes, mono-, di- or trisubstituted glycerides, for slowing down the penetration of water or of aqueous fluids into the pharmaceutical preparation.

The technical preparation of the tablets may lead to introducing:

lubricants such as magnesium stearate, stearic acid, glyceryl monostearate, polyoxyethylene glycols having a molecular weight of from 400 to 7,000,000, hydrogenated castor oil, glyceryl behenate, mono-, di- or trisubstituted glycerides, flow agents such as colloidal silica or any other silica, and binders, buffers, absorbing agents, as well as any other pharmaceutically acceptable additive.

The tablets of the invention may be produced in the following way: powders and/or granulates are mixed using current production technologies and thus with a production process which may be industrialized immediately.

The pharmaceutical tablet containing two or three layers is obtained according to tableting processes that are very commonly used and known to those skilled in the art.

For example, the tablets may be produced using rotary presses capable of producing "multi-layer" tablets.

Normally, the working compression force ranges from 7 to 50 KN (or kilonewtons) and, according to the processes which will be described in greater detail in the examples, tablets containing two or three layers having a cylindrical, lenticular, spheroidal or ovoid shape which makes them easy to administer and to swallow, are obtained.

Depending on the amount of active substance which is conveyed, each layer of the tablet may have a different thickness ranging from 0.2 to 8 mm, but preferably from 1 mm to 4 mm.

A coating made of polymer materials, whose aim is to afford simple protection or alternatively a slowing-down at the start of the release of the active substance conveyed in the pharmaceutical preparation, may also be applied to this pharmaceutical prepartion. The coating may be soluble in acidic solution or alternatively permeable, so t activation of the tablet (release of the active substance) only after a predetermined time period.

According to another embodiment of the invention, a soluble coating containing alfuzosin hydrochloride may be applied so as to allow immediate release of some of the active substance on contact with the gastric juices.

The coating may be applied by standard methods known to those skilled in the art using organic or aqueous solutions.

On contact with gastric juices and/or fluids of the gastrointestinal tract, the tablet rapidly increases in volume, taking the structure shown in FIG. 2.

This increase in volume may be determined and limited to a single layer or to several layers of the tablet; this increase in volume, as well as the rate at which this phenomenon takes place, may be monitored and evaluated precisely by direct measurement or by a video microscope coupled to a computer. The measurement is performed by a special video analysis programme.

The tablet is characterized in that the volume of at least one of the layers increases, at the end of 2 hours, by 1.5 times and preferably by at least 3 times relative to the initial volume.

By this method, it is possible to study the behaviour "in vitro" of various preparations (described in the examples of the Application) and thus to design pharmaceutical preparations capable of satisfying the required morphological qualities, as well as of optimizing the preparation of each of the said layers so as to obtain the morphological behaviour which satisfies the requested aim. This type of analysis thus makes it possible to model the "in vivo" behaviour of the pharmaceutical preparation on contact with biological fluids. It is also possible to program, within a determined time period, the release of the active substance conveyed in the pharmaceutical preparation.

The pharmaceutical compositions of the present invention may be in the form of tablets or small tablets or gelatin capsules comprising small tablets.

At least two small tablets may also be combined in the same pharmaceutical composition. They may be packaged in a common envelope, for example in a wafer capsule or in a gelatin capsule.

When the pharmaceutical composition consists of small tablets, each of these may have a different or identical composition.

The examples which follow are intended to illustrate the invention.

EXAMPLE 1:

Preparation of a series of tablets (5000) based on alfuzosin hydrochloride.

1A: Preparation of the granulate containing the active substance

A granulate is prepared, according to the process described below, which is used for the preparation of the layer 2 of FIG. 1 containing 10.0 mg of alfuzosin hydrochloride and having the following unit composition:

| | |
|---|---|
| Alfuzosin hydrochloride | 10.00 mg |
| Mannitol | 10.00 mg |
| Hydroxypropylmethylcellulose USP 2208 | 10.00 mg |
| Polyvinylpyrrolidone | 3.20 mg |
| Microcrystalline cellulose | 65.00 mg |
| Magnesium stearate | 1.00 mg |
| Colloidal silica | 1.25 mg |
| Total | 100.45 mg |

The manufacturing process consists in preparing a granulate by mixing together the amounts of active substance required, mannitol, microcrystalline cellulose and hydroxypropylmethylcellulose. The uniform powder mixture is moistened uniformly with an alcoholic solution based on 10% w/v polyvinyl-pyrrolidone and is then dried to a predetermined percentage of residual moisture in a fluidized-air bed at 40–45° C. The dried granulate is calibrated and placed in a powder mixer with magnesium stearate and colloidal silica and it is then mixed until homogeneous.

1B: Preparation of the granulate constituting layer 1 which swells

An amount of granulate required to obtain 5000 layers which swell, layer 1 of FIG. 1, were prepared, each layer having the following percentage composition:

| | |
|---|---|
| Hydroxypropylmethylcellulose | 79.75% |
| Hydrogenated castor oil | 13.50% |
| Yellow iron oxide | 0.25% |
| Ethylcellulose | 5.00% |
| Magnesium stearate | 1.00% |
| Silica gel | 0.50% |
| Total | 100.00% |

The manufacturing process consists of the preparation of a granulate obtained by mixing the required amounts of hydroxypropylmethylcellulose, hydrogenated castor oil and iron oxide; the uniform powder mixture is moistened with an alcoholic solution based on 10% w/v ethylcellulose and the uniformly moistened mass is dried in a fluidized-air bed at 40–45° C. The granulate, dried to a predetermined percentage of moisture, is calibrated and placed in a powder mixer with magnesium stearate and colloidal silica and it is mixed until homogeneous.

1C: Preparation of the granulate constituting the third layer 3 which acts as a barrier An amount of granulate required to obtain 5000 barrier layers is prepared, layer 3 of FIG. 1, each layer having the following percentage composition:

| | |
|---|---|
| Hydroxypropylmethylcellulose | 76.00% |
| Hydrogenated castor oil | 18.60% |
| Polyvinylpyrrolidone | 3.15% |
| Yellow iron oxide | 0.10% |
| Magnesium stearate | 0.70% |
| Colloidal silica | 1.45% |
| Total | 100.00% |

The manufacturing process consists in mixing the required amounts of hydroxypropylmethylcellulose, hydrogenated castor oil and yellow iron oxide; the homogeneous powder mixture is moistened with a solution based on 10% w/v polyvinylpyrrolidone in ethanol and the wet mass is dried in a fluidized-air bed at 40–45° C. The granulate, dried to a predetermined percentage of residual moisture, is calibrated and placed in a powder mixer with magnesium stearate and colloidal silica and mixed until homogeneous.

1D: Preparation of tablets containing three layers (by compression)

The granulates obtained are loaded into the three supply hoppers of a rotary multi-layer press capable of producing three-layer tablets. The granulate described in point 1B is loaded into the first hopper, the granulate according to the description of point 1A is loaded into the second hopper and the granulate according to the description of point 1C is loaded into the third hopper; granulates 1B and 1C may be inverted in the hoppers.

The multi-layer press is equipped with flat circular bevelled punches having a diameter of 8 mm. The machine is adjusted to produce three-layer tablets consisting of a first amount of 100 mg of layer 1 for a thickness of about 1.7 mm, a second amount of 100.45 mg of granulate containing the active substance (equivalent to 10.0 mg of alfuzosin hydrochloride) and a third amount of 150 mg of layer 3 for a thickness of about 3.3 mm. Working according to the above description, three-layer tablets having an average weight of 350.45 mg and containing 10.0 mg of alfuzosin hydrochloride are produced.

1E: Dissolution test

In order to evaluate the release properties of the complete tablets, the vane machine (described in USP XXIII) is used, working at 100 rpm and using as dissolution liquid a 0.01M HCl solution at 37° C. The release of the active substance is monitored by UV spectrophotometric determination at 330 nm using a sampling and automatic reading system.

The results of the tests carried out are given in Table 1.

TABLE 1

| Time (hours) | % released |
|---|---|
| 1 | 16.0 |
| 2 | 25.0 |
| 3 | 32.0 |
| 4 | 37.0 |
| 6 | 48.0 |
| 8 | 57.0 |
| 10 | 66.0 |
| 12 | 74.0 |
| 16 | 88.0 |

TABLE 1-continued

| Time (hours) | % released |
|---|---|
| 20 | 95.0 |
| 24 | 98.0 |

A controlled release of the active substance is obtained in about 20 hours.

1F: Swelling test

The test is carried out under the same experimental conditions as the dissolution test. The tablets are taken from the dissolution medium at regular intervals and their volume and the sizes of the various layers are measured with a video-microscope coupled to an image-analysis system. The results of the tests carried out are given in Table 2.

TABLE 2

| Swelling time (hours) | Volume (layer 2 + layer 3) (%) | Volume of layer 1 (%) |
|---|---|---|
| 0 | 100.0 | 100.0 |
| 0.5 | 142.0 | 211.1 |
| 1 | 152.7 | 271.0 |
| 1.5 | 175.2 | 302.6 |
| 2 | 161.8 | 399.5 |
| 3 | 182.7 | 483.7 |
| 4 | 196.0 | 534.0 |
| 5 | 199.4 | 609.8 |
| 6 | 195.7 | 727.9 |
| 7 | 166.8 | 809.9 |
| 8 | 138.9 | 851.0 |
| 10 | 139.9 | 937.5 |

It may be noted that, in the tablets, layer 1 increases considerably in volume, up to 9 times its initial volume. This phenomenon is very evident if it is related to the increase in volume of the other two layers, layer 2 and layer 3, which cumulatively swell to about 2-fold. In addition, layer 1 increases in volume at a rate which is considerably higher than that of the other layers.

EXAMPLE 2

Preparation of a series of tablets (10,000) as reported in FIGS. 1 and 2, containing alfuzosin hydrochloride as active substance.

2A: Preparation of the granulate containing the active substance

A granulate is prepared, according to the process described in Example 1A, which is used in the preparation of the layer 2 of FIG. 1 containing 7.5 mg of alfuzosin hydrochloride, and having the following unit composition:

| | |
|---|---|
| Alfuzosin hydrochloride | 7.50 mg |
| Mannitol | 10.00 mg |
| Hydroxypropylmethylcellulose | 10.00 mg |
| Polyvinylpyrrolidone | 3.20 mg |
| Microcrystalline cellulose | 65.00 mg |
| Magnesium stearate | 1.00 mg |
| Colloidal silica | 1.25 mg |
| Total | 97.95 mg |

2B: Preparation of the granulate constituting the first layer 1 which swells An amount of granulate required to obtain 10,000 layers which swell, layer 1 of FIG. 1, is prepared according to the process described in Example 1B, each layer having the following percentage unit composition:

| | |
|---|---|
| Hydroxypropylmethylcellulose | 79.75% |
| Hydrogenated castor oil | 13.50% |
| Ethylcellulose | 5.00% |
| Iron oxide | 0.25% |
| Magnesium stearate | 1.00% |
| Colloidal silica | 0.50% |
| Total | 100.00% |

2C: Preparation of the granulate constituting the third layer 3

An amount of granulate required to obtain 10,000 barrier layers, layer 3 of FIG. 1, is prepared according to the process described in Example 1C, each layer having the following percentage unit composition:

| | |
|---|---|
| Hydroxypropylmethylcellulose | 76.00% |
| Hydrogenated castor oil | 18.60% |
| Polyvinylpyrrolidone | 3.15% |
| Yellow iron oxide | 0.10% |
| Magnesium stearate | 1.45% |
| Colloidal silica | 0.70% |
| Total | 100.00% |

2D: Preparation of the three-layer tablets (by compression)

The granulates obtained according to Examples 2A, 2B and 2C are loaded into the three supply hoppers of a rotary press with respective amounts of 100 mg of granulate for layer 1 for a thickness of 1.75 mm, 97.95 mg of granulate containing the active substance (corresponding to 7.5 mg of alfuzosin hydrochloride) for layer 2 and 150 mg for layer 3 for a thickness of 3.3 mm. By working in the manner described above, three-layer tablets having an average weight of 347.95 mg and containing 7.5 mg of active substance are obtained.

2E: Dissolution test

The dissolution tests are carried out according to the process described in Example 1E.

The results are given in Table 3.

TABLE 3

| Time (hours) | % released |
|---|---|
| 1 | 15.1 |
| 2 | 24.4 |
| 4 | 37.7 |
| 6 | 48.0 |
| 8 | 57.6 |
| 10 | 66.0 |
| 12 | 74.2 |
| 14 | 82.2 |
| 16 | 89.1 |
| 18 | 94.8 |
| 20 | 98.6 |

It may be noted that the controlled release of the active substance takes place over about 20 hours.

2F: Swelling test

The swelling tests are carried out according to the process described in Example 1F. The results are given in Table 4.

TABLE 4

| Time (hours) | Volume (layer 2 + layer 3) (%) | Volume of layer 1 (%) |
| --- | --- | --- |
| 0 | 100.0 | 100.0 |
| 0.5 | 137.6 | 233.2 |
| 1 | 142.3 | 305.1 |
| 1.5 | 150.4 | 338.5 |
| 2 | 142.3 | 412.4 |
| 3 | 167.1 | 435.2 |
| 4 | 139.2 | 526.5 |
| 6 | 132.0 | 665.0 |
| 8 | 129.9 | 715.1 |

It may be noted that in the tablets prepared, the volume of layer 1 increases considerably, by up to 7 times the initial volume; layer 2 and layer 3 increase by up to one and a half times. In addition, layer 1 increases in volume at a rate which is very much higher than that of the other two layers.

EXAMPLE 3

Preparation of a series of tablets (10,000) containing alfuzosin hydrochloride as active substance 3A: Preparation of the granulate containing the active substance.

A granulate used in the preparation of layer 2 is prepared according to the process described in Example 1A, this granulate containing 10.0 mg of alfuzosin hydrochloride and having the following unit composition:

| | |
| --- | --- |
| Alfuzosin hydrochloride | 10.00 mg |
| Mannitol | 10.00 mg |
| Hydroxypropylmethylcellulose | 10.00 mg |
| Polyvinylpyrrolidone | 3.20 mg |
| Microcrystalline cellulose | 65.00 mg |
| Magnesium stearate | 1.00 mg |
| Colloidal silica | 1.25 mg |
| Total | 100.45 mg |

3B: Preparation of the granulate constituting the first layer 1 which swells

An amount of granulate required to obtain 10,000 layers which swell, layer 1 of FIG. 1, is prepared according to the process described, each layer having the following percentage composition:

| | |
| --- | --- |
| Hydroxypropylmethylcellulose | 75.00% |
| Glyceryl behenate | 13.40% |
| Polyvinylpyrrolidone | 5.00% |
| Iron oxide | 0.10% |
| Polyvinylpyrrolidone | 5.00% |
| Magnesium stearate | 1.00% |
| Colloidal silica | 0.50% |
| Total | 100.00% |

3C: Preparation of the granulate constituting the third layer 3

An amount of granulate required to obtain 10,000 layers, layer 3 of FIG. 1, is prepared according to the process described in Example 1C, each layer having the following percentage composition:

| | |
| --- | --- |
| Hydroxypropylmethylcellulose | 76.00% |
| Hydrogenated castor oil | 18.60% |
| Polyvinylpyrrolidone | 3.15% |
| Yellow iron oxide | 0.10% |
| Magnesium stearate | 1.45% |
| Colloidal silica | 0.70% |
| Total | 100.00% |

3D: Preparation of three-layer tablets (by compression)

The granulates obtained as described in Examples 3A, 3B and 3C are loaded into the three supply hoppers of a rotary press with respective amounts of 100 mg of granulate for layer 1, 100.45 mg of granulate containing the active substance for layer 2 and 150 mg for layer 3. By working in the manner described above, three-layer tablets having an average weight of 350.45 mg and containing 10.0 mg of active substance are obtained.

3E: Dissolution test

The dissolution tests are carried out according to the process described in Example 1E.

The results of the tests carried out are given in Table 5.

TABLE 5

| Time (hours) | % released |
| --- | --- |
| 1 | 19.0 |
| 2 | 27.8 |
| 4 | 41.7 |
| 6 | 53.4 |
| 8 | 64.7 |
| 10 | 75.6 |
| 12 | 84.6 |
| 14 | 90.9 |
| 16 | 95.1 |
| 18 | 97.8 |
| 20 | 99.4 |

The controlled release of the active substance takes place over about 18 hours.

3F: Swelling test

The swelling tests are carried out according to the process described in Example 1F.

The results of the tests carried out are given in Table 6.

TABLE 6

| Time (hours) | Volume (layer 2 + layer 3) (%) | Volume of layer 1 (%) |
| --- | --- | --- |
| 0 | 100.0 | 100.0 |
| 0.5 | 124.0 | 231.8 |
| 1 | 130.5 | 297.0 |
| 2 | 108.5 | 387.0 |
| 3 | 115.2 | 448.8 |
| 4 | 131.3 | 517.2 |
| 5 | 124.7 | 554.5 |
| 6 | 137.0 | 601.1 |
| 8 | 106.6 | 740.5 |

It may be noted that in the tablets prepared, the volume of layer 1 which swells increases considerably, by up to 7 times its initial volume; layer 2 and layer 3 only increase by 30–40% relative to the initial volume. In addition, the layer which swells increases in volume at a rate which is very much higher than that of the other two layers.

EXAMPLE 4

Preparation of a series of tablets (5000) based on alfuzosin hydrochloride.

4A: Preparation of the granulate containing the active substance

A granulate is prepared according to the process described below, which is used for the preparation of layer 2 of FIG. 1 containing 10.0 mg of alfuzosin hydrochloride and having the following unit composition:

| | |
|---|---|
| Alfuzosin hydrochloride | 10.00 mg |
| Lactose | 60.30 mg |
| Hydroxypropylmethylcellulose USP 2208 | 25.00 mg |
| Polyvinylpyrrolidone | 3.20 mg |
| Magnesium stearate | 1.00 mg |
| Colloidal silica | 0.50 mg |
| Total | 100.00 mg |

The manufacturing process consists in preparing a granulate by mixing the required amounts of active substance, of lactose, of polyvinylpyrrolidone and of hydroxypropylmethylcellulose. The uniform powder mixture is uniformly moistened with purified water and is then dried to a predetermined residual moisture percentage in a fluidized-air bed at 40–45° C. The dried granulate is calibrated and placed in a powder mixer with magnesium stearate and colloidal silica and is then mixed until homogeneous.

4B: Preparation of the granulate constituting layers 1 and 3 which swell and form a barrier An amount of granulate required to obtain 10,000 layers which swell and form a barrier, layers 1 and 3 of FIG. 1, is prepared, each layer having the following percentage composition:

| | |
|---|---|
| Hydroxypropylmethylcellulose USP 2208 | 40.00% |
| Lactose | 39.75% |
| Glyceryl behenate | 13.50% |
| Yellow iron oxide | 0.25% |
| Polyvinylpyrrolidone | 5.00% |
| Magnesium stearate | 1.00% |
| Colloidal silica | 0.50% |
| Total | 100.00% |

The manufacturing process consists in preparing a granulate obtained by mixing together the required amounts of hydroxypropylmethylcellulose, of lactose, of glyceryl behenate, of polyvinylpyrrolidone and of iron oxide; the uniform powder mixture is moistened with purified water. The uniformly moistened mass is dried in a fluidized-air bed at 40–45° C. The granulate, dried to a predetermined moisture percentage, is calibrated and placed in a powder mixer with magnesium stearate and colloidal silica and it is mixed until homogeneous.

4C: Preparation of three-layer tablets (by compression)

The granulates obtained are loaded into the three supply hoppers of a rotary multilayer press capable of producing three-layer tablets. The granulate described in point 4B is loaded into the first and third hoppers; the granulate according to the description of point 4A is loaded into the second hopper.

The multi-layer press is equipped with flat circular bevelled punches having a diameter of 8 mm. The machine is adjusted to produce three-layer tablets consisting of a first amount of 100 mg of layer 1 or 3 for a thickness of about 1.7 mm, a second amount of 100 mg of granulate containing the active substance and a third amount of 100 mg of layer 1 or 3 for a thickness of about 1.7 mm. By working according to the above description, three-layer tablets having an average weight of 300 mg and containing 10.0 mg of alfuzosin hydrochloride are produced.

EXAMPLE 5

Preparation of a series of tablets (5000) based on alfuzosin hydrochloride.

5A: Preparation of the granulate containing the active substance

A granulate is prepared according to the process described in Example 4A, this granulate being used in the preparation of layer 2 of FIG. 1 containing 15 mg of alfuzosin hydrochloride and having the following unit composition:

| | |
|---|---|
| Alfuzosin hydrochloride | 15.00 mg |
| Lactose | 55.30 mg |
| Hydroxypropylmethylcellulose USP 2208 | 25.00 mg |
| Polyvinylpyrrolidone | 3.20 mg |
| Magnesium stearate | 1.00 mg |
| Colloidal silica | 0.50 mg |
| Total | 100.00 mg |

5B: Preparation of the granulate constituting layers 1 and 3 which swell and form a barrier An amount of granulate required to obtain 10,000 layers which swell and form a barrier, layers 1 and 3 of FIG. 1, is prepared, each layer corresponding to the composition and to the manufacturing process described in Example 4B.

5C: Preparation of three-layer tablets (by compression)

By working in the manner described above (Example 4C), three-layer tablets containing 15.0 mg of active substance are obtained with the granulates described in Examples 5A and 5B.

EXAMPLE 6

Preparation of a series of tablets (5000) based on alfuzosin hydrochloride.

6A: Preparation of the granulate containing the active substance

A granulate is prepared according to the process described below, this granulate being used in the preparation of layer 2 of FIG. 1 containing 10 mg of alfuzosin hydrochloride and having the following unit composition:

| | |
|---|---|
| Alfuzosin hydrochloride | 10.00 mg |
| Microcrystalline cellulose | 33.80 mg |
| Mannitol | 10.00 mg |
| Hydroxypropylmethylcellulose USP 2208 | 40.00 mg |
| Polyvinylpyrrolidone | 5.00 mg |
| Magnesium stearate | 1.00 mg |
| Colloidal silica | 0.20 mg |
| Total | 100.00 mg |

The manufacturing process consists in preparing a granulate by mixing together the required amounts of active substance, of cellulose, of polyvinylpyrrolidone, of mannitol and of hydroxypropylmethylcellulose. The uniform powder mixture is moistened uniformly with purified water and is then dried to a predetermined residual moisture percentage in a fluidized-air bed at 40–50° C. The dried granulate is calibrated and placed in a powder mixer with magnesium stearate and colloidal silica until homogeneous.

6B: Preparation of the granulate constituting layers 1 and 3 which swell and form a barrier An amount of granulate required to obtain 10,000 layers which swell and form a barrier, layers 1 and 3 of FIG. 1, is prepared, each layer having the following percentage composition:

| | |
|---|---|
| Hydroxypropylmethylcellulose USP 2208 | 45.00% |
| Lactose | 28.60% |
| Microcrystalline cellulose | 20.00% |
| Yellow iron oxide | 0.20% |
| Polyvinylpyrrolidone | 5.00% |
| Magnesium stearate | 1.00% |
| Colloidal silica | 0.20% |
| Total | 100.00% |

The manufacturing process is identical to that of Example 4B, the microcrystalline cellulose being added in place of the glyceryl behenate.

6C: Preparation of three-layer tablets (by compression)

By working in the manner described above (Example 4C), three-layer tablets containing 10.0 mg of active substance are obtained with 100 mg, for each of the layers, of granulates described in Examples 6A and 6B, layers 1 and 3 having a thickness of about 1.8 mm.

EXAMPLE 7

Preparation of a series of tablets (5000) based on alfuzosin hydrochloride.

7A: Preparation of the granulate containing the active substance

A granulate is prepared according to the process described below, this granulate being used in the preparation of layer 2 of FIG. 1 containing 15 mg of alfuzosin hydrochloride and having the following unti composition:

| | |
|---|---|
| Alfuzosin hydrochloride | 15.00 mg |
| Microcrystalline cellulose | 28.80 mg |
| Mannitol | 10.00 mg |
| Hydroxypropylmethylcellulose USP 2208 | 40.00 mg |
| Polyvinylpyrrolidone | 5.00 mg |
| Magnesium stearate | 1.00 mg |
| Colloidal silica | 0.20 mg |
| Total | 100.00 mg |

The manufacturing process is identical to that of Example 6A.

7B: Preparation of the granulate constituting layers 1 and 3 which swell and form a barrier An amount of granulate required to obtain 10,000 layers which swell and form a barrier, layers 1 and 3 of FIG. 1, is prepared, each layer corresponding to the composition and to the manufacturing process described in Example 6B.

7C: Preparation of three-layer tablets (by compression)

By working in the manner described above (Example 6C), three-layer tablets containing 15.0 mg of active substance are obtained with the granulates described in Examples 7A and 7B.

EXAMPLE 8

Preparation of a series of tablets (5000) based on alfuzosin hydrochloride.

8A: Preparation of the granulate containing the active substance

A granulate is prepared, which is used in the preparation of layer 2 of FIG. 1, containing 10 mg of alfuzosin hydrochloride, with a composition identical to that described in Example 6A and according to the same process.

8B: Preparation of the granulate constituting layers 1 and 3 which swell and form a barrier An amount of granulate required to obtain 10,000 layers which swell and form a barrier, layers 1 and 3 of FIG. 1, is prepared, each layer having the following percentage composition:

| | |
|---|---|
| Hydroxypropylmethylcellulose USP 2208 | 35.00% |
| Lactose | 34.50% |
| Microcrystalline cellulose | 23.90% |
| Yellow iron oxide | 0.40% |
| Polyvinylpyrrolidone | 5.00% |
| Magnesium stearate | 1.00% |
| Colloidal silica | 0.20% |
| Total | 100.00% |

The manufacturing process is identical to that of Example 6B.

8C: Preparation of three-layer tablets (by compression)

The granulates obtained are loaded into the three supply hoppers of a rotary multi-layer press capable of producing three-layer tablets. The granulate described in point 8B is loaded into the first and third hoppers; the granulate according to the description of point 8A is loaded into the second hopper.

The multi-layer press is equipped with flat circular bevelled punches having a diameter of 8 mm. The machine is adjusted to produce three-layer tablets whose outer layers consist of 100 mg and 150 mg of the granulate described in point 8B and corresponding respectively to a thickness of about 1.7 mm for one of them and 2.7 mm for the other. The inner layer is composed of 100 mg of granulate containing the active substance (equivalent to 10.0 mg of alfuzosin hydrochloride). By working according to the above description in point 7C, three-layer tablets having an average weight of 350 mg and containing 10.0 mg of alfuzosin hydrochloride are produced.

EXAMPLE 9

Preparation of a series of tablets (5000) based on alfuzosin hydrochloride.

9A: Preparation of the granulate containing the active substance

A granulate is prepared, which is used in the preparation of layer 2 of FIG. 1, containing 15 mg of alfuzosin hydrochloride, with a composition identical to that described in Example 7A and according to the same process.

9B: Preparation of the granulate constituting layers 1 and 3 which swell and form a barrier An amount of granulate required to obtain 10,000 layers which swell and form a barrier, layers 1 and 3 of FIG. 1, is prepared, each layer corresponding to the composition and to the manufacturing process described in Example 8B.

9C: Preparation of the three-layer tablets (by compression)

By working in the manner described above (Example 8C), three-layer tablets containing 15.0 mg of active substance and having an average weight of 350 mg are obtained with 100 mg of granulate described in Example 9A and, for the outer layers, 100 and 150 mg of granulate described in point 9B corresponding respectively to a thickness of about 1.8 mm for one and 2.7 mm for the other.

EXAMPLE 10

Preparation of a series of tablets (5000) based on alfuzosin hydrochloride.

10A: Preparation of the granulate containing the active substance

A granulate is prepared, which is used in the preparation of layer 2 of FIG. 1, containing 7.5 mg of alfuzosin hydrochloride, with a composition which is identical to that described in Example 2A and according to the same process.

10B: Preparation of the granulate constituting layers 1 and 3 which swell and form a barrier An amount of granulate required to obtain 10,000 layers which swell and form a barrier, layers 1 and 3 of FIG. 1, is prepared, each layer corresponding to the composition and to the manufacturing process described in Example 4B.

10C: Preparation of the three-layer tablets (by compression)

By working in the manner described above (Example 8C), three-layer tablets containing 7.5 mg of active substance and having an average weight of 350 mg are obtained, with 100 mg of granulate described in Example 10A and, for the outer layers, 100 and 150 mg of granulate described in point 10B, corresponding respectively to a thickness of about 1.8 mm for one and 5 2.7 mm for the other.

EXAMPLE 11

Preparation of a series of tablets (5000) based on alfuzosin hydrochloride.

11A: Preparation of the granulate containing the active substance

A granulate containing 10 mg of alfuzosin hydrochloride is prepared, with a composition which is identical to that described in Example 4A and according to the same process.

11B: Preparation of the granulate constituting layer 1 which swells

An amount of granulate required to obtain 10,000 layers which swell is prepared. Each layer corresponds to the composition and to the manufacturing process described in Example 4B.

11C: Preparation of the two-layer tablets (by compression)

By working in the manner described above (Example 8C), the granulates obtained, 100 mg of granulate described in Example 10A and, for the outer layer, 150 mg of granulate described in point 10B, are loaded into two supply hoppers of a rotary multi-layer press capable of producing two-layer tablets.

What is claimed is:

1. A pharmaceutical tablet for oral administration and for the controlled release of alfuzosin hydrochloride into the proximal segments of the gastrointestinal tract, the tablet comprising:
    a) a first layer having the property of swelling considerably and quickly on contact with aqueous biological fluids, the first layer being produced by compression of a mixture or of a granulate comprising a hydrophilic polymer constituting from 5.0 to 90% of the weight of the first layer,
    b) a second layer adjacent to the first layer containing the alfuzosin hydrochloride, the second layer being formulated with a hydrophilic polymer and with an auxiliary substance to give the preparation suitable properties of compressibility and in order to allow the release of alfuzosin hydrochloride within a predetermined time period,
    c) and optionally a third layer adjacent to the second layer comprising a hydrophilic polymer which gels and/or swells and which may optionally be broken down and has a barrier function which modifies the release of the alfuzosin hydrochloride from the second layer, the third layer being primarily highly impervious to passage of the active substance.

2. The tablet according to claim 1, wherein at least one of the layers comprises an hydrophilic product and/or an excipient.

3. The tablet according to claim 2, wherein the hydrophilic excipient is crosslinked polyvinylpyrrolidone, hydroxypropylcellulose or hydroxypropylmethylcellulose having a molecular weight from 1,000 to 100,000, crosslinked sodium carboxymethylcellulose, carboxymethyl starch or its salts, or divinylbenzene/potassium methyacrylate copolymer.

4. The tablet according to claim 2, wherein the hydrophilic excipient constitutes from 1 to 50% of the weight of the layer.

5. The tablet according to claim 1, wherein the third layer has an identical composition to that of the first layer and the same functional properties.

6. The tablet according to claim 5, wherein the first and third layers differ in the amount applied to the second layer and their thickness.

7. The tablet according to claim 1, wherein, on contact with an aqueous liquid, at least one of the layers of the tablet increases by at least 1.5 times relative to the initial volume after two hours.

8. Tablet according to claim 1, wherein the hydrophilic polymer is hydroxymethylcellulose, hydroxyethylcellulose, hydroxypropylmethylcellulose having a molecular weight of from 1000 to 4,000,000, hydroxypropylcellulose having a molecular weight of from 2000 to 2,000,000, a carboxyvinyl polymer, a chitosan, a mannan, a galactomannan, a xanthan, a carrageenan, an amylose, an alginic acid, a pectin, an acrylate, a methacrylate, an acrylic/methacrylic copolymer, a polyanhydride, a polyamino acid, a poly(methyl vinyl ether/maleic anhydride) polymer, a polyvinyl alcohol, a glucan, a scleroglucan, a carboxymethylcellulose, an ethylcellulose, or a methylcellulose.

9. The tablet according to claim 1, wherein the second layer containing the active substance comprises 5 to 90% by weight of the hydrophilic polymer.

10. The tablet according to claim 1, wherein the third layer contains alfuzosin hydrochloride.

11. The tablet according to claim 1, wherein the amount of alfuzosin hydrochloride in the tablet ranges from 2.5 to 50 mg.

12. The tablet according to claim 1, further comprising a surfactant which is sodium lauryl, sulphate, sodium ricinoleate, sodium tetradecyl sulphate, sodium dioctyl, sulphosuccinate, cetomacrogol, poloxamer, glyceryl monostearate, a polysorbate, sorbitan monolaurate, or a lecithin.

13. The tablet according to claim 1, further comprising an hydrophilic diluent which is mannitol, lactose, a starch, sorbitol, xylitol, microcrystalline cellulose or a substance which promotes the penetration of water and/or an aqueous fluid into the layers.

14. The tablet according to claim 1, further comprising an hydrophobic diluent which is glyceryl monostearate, a palmitate, an hydrogenated plant oil or a wax used for slowing down the penetration of water and/or of aqueous fluids into the second layer containing the active substance and into the first and third layers.

15. The tablet according to claim 1, wherein the layers of the tablet have different thicknesses ranging from 0.2 mm to 8 mm.

16. The tablet according to claim 1, wherein the tablet is compressed at a pressure that ranges from 7 to 50 KN.

17. The tablet according to claim 1, wherein the tablet is covered with a coating which may optionally contain alfuzosin hydrochloride.

18. A pharmaceutical composition comprising one or more tablets according to claim 1.

19. The tablet according to claim 1, wherein the hydrophilic polymer constitutes from 10 to 85% of the weight of the first layer.

20. The tablet according to claim 2, wherein the hydrophilic excipient constitutes from 10 to 30% of the weight of the layer.

21. The tablet according to claim 1, wherein, on contact with an aqueous liquid, at least one of the layers of the tablet increases by at least 3 times relative to the initial volume after two hours.

22. The tablet according to claim 1, wherein the second layer comprises 10 to 85% by weight of the hydrophilic polymer.

23. The tablet according to claim 1, wherein a) the first layer consists of by weight:

| | |
|---|---|
| hydroxypropylmethylcellulose | 79.75% |
| hydrogenated castor oil | 13.50% |
| yellow iron oxide | 0.25% |
| ethylcellulose | 5.00% |
| magnesium stearate | 1.00% |
| silica gel | 0.50% | b) the second layer consists of by weight:

| | |
|---|---|
| alfuzosin hydrochloride | 10.00 mg |
| mannitol | 10.00 mg |
| hydroxypropylmethylcellulose | 10.00 mg |
| polyvinylpyrrolidone | 3.20 mg |
| microcrystalline cellulose | 65.00 mg |
| magnesium stearate | 1.00 mg |
| colloidal silica | 1.25 mg | c) and the third layer consists of by weight:

| | |
|---|---|
| hydroxypropylmethylcellulose | 76.00% |
| hydrogenated castor oil | 18.60% |
| polyvinylpyrrolidone | 3.15% |
| yellow iron oxide | 0.10% |
| magnesium stearate | 0.70% |
| colloidal silica | 1.45%. |

* * * * *

UNITED STATES PATENT AND TRADEMARK OFFICE
CERTIFICATE OF CORRECTION

PATENT NO. : 6,149,940
DATED : November 21, 2000
INVENTOR(S) : Maggi et al.

It is certified that error appears in the above-identified patent and that said Letters Patent is hereby corrected as shown below:

<u>Title page,</u>
Item [73], correct the name of the Assignee from "Jagotec AB" to -- Jagotec AG --.

Signed and Sealed this

Thirtieth Day of April, 2002

*Attest:*

JAMES E. ROGAN
*Director of the United States Patent and Trademark Office*

*Attesting Officer*